USO11346929B2

(12) United States Patent
Vignon et al.

(10) Patent No.: US 11,346,929 B2
(45) Date of Patent: May 31, 2022

(54) SYSTEMS AND METHODS FOR ULTRAFAST ULTRASOUND IMAGING

(71) Applicant: KONINKLIJKE PHILIPS N.V., Eindhoven (NL)

(72) Inventors: Francois Guy Gerard Marie Vignon, Andover, MA (US); Bo Zhang, Paris (FR); Jean-Luc Francois-Marie Robert, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 242 days.

(21) Appl. No.: 16/478,165

(22) PCT Filed: Jan. 16, 2018

(86) PCT No.: PCT/EP2018/050948
§ 371 (c)(1),
(2) Date: Jul. 16, 2019

(87) PCT Pub. No.: WO2018/130704
PCT Pub. Date: Jul. 19, 2018

(65) Prior Publication Data
US 2019/0353764 A1 Nov. 21, 2019

(30) Foreign Application Priority Data

Jan. 16, 2017 (EP) .................................... 17305046

(51) Int. Cl.
*G01S 7/52* (2006.01)
*A61B 8/14* (2006.01)
(Continued)

(52) U.S. Cl.
CPC ............ *G01S 7/52085* (2013.01); *A61B 8/14* (2013.01); *A61B 8/4488* (2013.01); *A61B 8/488* (2013.01);
(Continued)

(58) Field of Classification Search
CPC ... G01S 7/52085; G01S 7/5202–52022; A61B 8/4488; A61B 8/5246
See application file for complete search history.

(56) References Cited

U.S. PATENT DOCUMENTS 6,363,033 B1 * 3/2002 Cole .................... G01S 7/52017
367/138
6,803,876 B2 * 10/2004 Erkocevic-Pribic .........................
G01S 13/225
342/159
(Continued)

FOREIGN PATENT DOCUMENTS

CN 104188687 A * 12/2014
JP 2007222390 A 9/2007
(Continued)

OTHER PUBLICATIONS

Avdal, et al., "Effects of Reverberations and Clutter Filtering in Pulsed Doppler Using Sparse Sequences", IEEE Transactions on Ultrasonics, Ferroelectrics, and Frequency Control, vol. 62, No. 5, May 2015, pp. 828-838.
(Continued)

*Primary Examiner* — Keith M Raymond
*Assistant Examiner* — Nyrobi Celestine

(57) ABSTRACT

A method in accordance with the present disclosure may include transmitting a plurality of ultrasound pulses toward a medium from a transducer array, wherein the plurality of ultrasound pulses includes a sequence of a Doppler burst (10-1, 10-2) comprising a plurality of unfocused first pulses (12) and a B-mode burst comprising one or more second pulses (13). The method may further include detecting echoes responsive to the transmitted sequence, wherein the detecting includes simultaneously detecting, within a field of view, FOV, of the array, a set (14-1, 14-2) of first echoes responsive to the plurality of unfocused first pulses (12),
(Continued)

generating Doppler data from signals representative of the set (14-1, 14-2) of first echoes, generating B-mode image data from signals representative of echoes responsive to the one or more second pulses (13), and simultaneously displaying the Doppler data and B-mode image data.

20 Claims, 9 Drawing Sheets

(51) Int. Cl.
A61B 8/00 (2006.01)
A61B 8/08 (2006.01)
(52) U.S. Cl.
CPC ........ A61B 8/5246 (2013.01); G01S 7/52022 (2013.01)

(56) References Cited

U.S. PATENT DOCUMENTS

| | | | |
|---|---|---|---|
| 9,295,446 B2* | 3/2016 | Li | A61B 8/5238 |
| 9,579,083 B2* | 2/2017 | Guracar | A61B 8/488 |
| 10,039,562 B2* | 8/2018 | Bailey | A61N 7/00 |
| 2003/0045795 A1 | 3/2003 | Bjaerum et al. | |
| 2009/0326379 A1 | 12/2009 | Daigle et al. | |
| 2012/0095341 A1 | 4/2012 | Shiki et al. | |
| 2019/0069803 A1* | 3/2019 | Bailey | A61B 8/0833 |
| 2019/0200961 A1* | 7/2019 | Specht | A61B 8/4488 |

FOREIGN PATENT DOCUMENTS

| | | | | |
|---|---|---|---|---|
| JP | 2011254862 A | 12/2011 | | |
| WO | WO-2009010918 A2 * | 1/2009 | ......... | G01S 15/8961 |

OTHER PUBLICATIONS

Kirkhorn, et al., "A New Technique for Improved Spatial Resolution in High Frame Rate Color Doppler Imaging", 2003 IEEE Ultrasonics Symposium, pp. 1947-1950.
International Search Report and Written Opinion for International Application No. PCT/EP2018/050948, filed Jan. 16, 2018, 21 pages.
Bercoff, et al., "Ultrafast Compound Doppler Imaging: Providing Full Blood Flow Characterization", IEEE Transactions on Ultrasonics, Ferroelectrics, and Frequency Control, vol. 58, No. 1, Jan. 2011, pp. 134-147.
Richy, et al., "Blood Velocity Estimation Using Compressive Sensing", IEEE Transactions on Medical Imaging, vol. 32, No. 11, Nov. 2013, pp. 1979-1988.
Zhang, et al., "Dual-Domain Compressed Beamforming for Medical Ultrasound Imaging", 2015 IEEE International Ultrasonics Symposium Proceedings, Conference Paper, Oct. 2014, 5 pages.
Lorintiu, et al., "Compressed Sensing Doppler Ultrasound Reconstruction Using Block Sparse Bayesian Learning", IEEE Transactions on Medical Imaging, vol. 35, No. 4, Apr. 2016, pp. 978-987.
Hoyos, et al., "Increasing the Dynamic Range of Synthetic Aperture Vector Flow Imaging", Medical Imaging 2014: Ultrasonic Imaging and Tomography, Proc. of SPIE, vol. 9040, pp. 904011-1 to 904011-12.
Poelma, et al., "Enhancing the dynamic range of Ultrasound Imaging Velocimetry using interleaved imaging", 10th International Symposium on Particle Image Velocimetry—PIV13, Delft, The Netherlands, Jul. 1-3, 2013, pp. 1-11.

* cited by examiner

SYSTEMS AND METHODS FOR ULTRAFAST ULTRASOUND IMAGING

RELATED APPLICATIONS

This application is the U.S. National Phase application under 35 U.S.C. § 371 of International Application No. PCT/EP2018/050948, filed on Jan. 16, 2018, which claims the benefit of European Application No. 17305046.9, filed Jan. 16, 2017. This application is hereby incorporated by reference herein.

TECHNICAL FIELD OF THE INVENTION

This application relates to ultrasound imaging, particularly ultrafast imaging techniques.

BACKGROUND OF THE INVENTION

Ultrasound imaging is typically performed by sequential insonification of a medium using focused beams. Each focused beam allows the reconstruction of a single image line. A typical 2D image is typically made of few tens or hundreds of lines and is created by the sequential reconstruction of each line in the image, the time for reconstructing each line depending on the image depth. Therefore, the time to build an image (e.g., frame rate) is dependent on the image depth and spatial resolution (e.g., number of image lines).

Ultrafast Doppler imaging is an emerging imaging technique in which samples are acquired for each location in the field of view at a temporal rate that enables Doppler estimation without aliasing. Unlike conventional imaging architectures which reconstruct images sequentially single line at a time from several transmits, ultrafast imaging transmits one or more pulses or waves to insonify the entire area of interest, and then relies on parallel processing of all image lines to generate the image data from the insonified field of view. As a result, one is able to obtain an image with significantly less signal transmissions, resulting in increased frame rates. Ultrafast imaging may be advantageously used for shear wave elastography and Doppler flow analysis. However, B-mode images generated from the same insonifications as used in ultrafast imaging may suffer from low SNR, low resolution, and grating lobe artifacts.

SUMMARY OF THE INVENTION

The invention proposes to improve ultrafast imaging acquisition in order to allow quality Doppler and B-mode images. This is accomplished by providing a pulse sequence that specifically interleaves continuous Doppler pulses with B-mode pulses in a manner that maintains the ultrafast paradigm while maximizing B-mode quality.

The invention is defined by the claims.

The method of the invention comprises: transmitting a plurality of ultrasound pulses toward a medium from a transducer array, wherein the plurality of ultrasound pulses includes a regularly repeated sequence comprising a Doppler burst of M unfocused first pulses and a B-mode burst of N second pulses, where M is 2 or more and N is 1 or more; detecting echoes responsive to the transmitted sequence, wherein the detecting includes sequentially detecting, within a field of view, FOV, of the array, first echoes each of which is responsive simultaneously to a set of M of the unfocused first pulses, and detecting a B-mode image frame comprising the echoes of multiple B-mode bursts in the sequence; generating Doppler data from signals representative of the first echoes; generating B-mode image data from signals representative of the B-mode image frame; and simultaneously displaying the Doppler data and B-mode image frame.

The case where M=1 is technically feasible, but is less preferred as it is currently considered it would be impractical.

All of the M first pulses in each Doppler burst may be transmitted within an intra-sample time interval which is less than one eighth of the wavelength of the unfocused pulses divided by the axial velocity of the flow being measured in the medium.

Successive Doppler bursts may be temporally spaced by an inter-sample time interval which is less than one quarter of their wavelength divided by the axial velocity of the flow being measured in the medium.

Successive Doppler bursts may be temporally spaced by an inter-sample time interval greater than one quarter of their wavelength divided by the axial velocity of the flow being measured in the medium, and the method may further comprise using anti-aliasing estimators such as cross-correlation tracking, phase unwrapping and/or compressive sensing, for generating the Doppler samples.

The B-mode bursts may include the maximum number of second pulses transmissible within the remaining interval of the inter-sample time interval between successive Doppler bursts.

The echoes from the M first pulses of the same Doppler burst may be used simultaneously to generate each Doppler sample, and each Doppler sample may be generated from a different Doppler burst. This is exemplified in FIG. 3.

The echoes from more than M successive first pulses may be used simultaneously to generate each Doppler sample, so that the echoes from two or more successive Doppler bursts are used to generate each Doppler sample. This is exemplified in FIG. 5. In this case all of the first pulses that are combined to generate each Doppler sample may still preferably be transmitted within an intra-sample time interval which is less than one eighth of the wavelength of the unfocused pulses divided by the axial velocity of the flow being measured in the medium.

The Doppler samples may be temporally spaced irregularly, and the method may include interpolating between the samples.

The first pulse transmitted in each burst of the first and/or the second pulses may be a conditioning pulse.

The B-mode second pulses may include focused pulses, wherein individual ones of the focused pulses are transmitted along an axial line within the FOV for generating B-mode image data associated with a single image line in the FOV, and wherein the repeated sequence generates the B-mode image frame comprising all the image lines in the FOV.

The second pulses may include one or more unfocused pulses.

M may greater than N.

According to some embodiments, the transmitting of the plurality of ultrasound pulses may include repeating the sequence to transmit multiple Doppler bursts and multiple B-mode bursts. In some embodiments, all of the first pulses in a given Doppler burst may be transmitted within an intra-sample time interval which is less than one eighth of a wavelength of the unfocused pulses divided by a velocity of the medium. In some embodiments, the sets of first echo signals associated with a given Doppler burst may be used to generate one Doppler sample, and successive Doppler bursts may be temporally spaced by an inter-sample time interval which is less than one quarter of the wavelength divided by the velocity. B-mode bursts which include B-mode pulses may be interleaved (e.g., transmitted between) the successive Doppler bursts. In some embodiments, the B-mode bursts may be configured to include a maximum number of second pulses transmittable within a remaining interval of the inter-sample time interval between successive Doppler bursts. In this manner, Doppler imaging may be performed in continuous or ultrafast mode while B-mode image data is obtained at higher resolutions and SNR and fewer artefacts than previously possible.

In some embodiments, only sets of first echo signals that are associated with a given Doppler burst may be used to generate a given Doppler sample. In some embodiments, sets of first echo signals associated with a plurality of Doppler burst may be used to generate one Doppler sample. In some embodiments, one or more sets of first echo signals may be used multiple times (e.g., coherently combined) for generating a plurality of Doppler samples. In other words, in some embodiments, two or more Doppler samples may be based, at least in part, on echo signals received responsive to the same Doppler burst. In some embodiments, the transmitting of ultrasound pulses may include transmitting a plurality of Doppler bursts temporally spaced by a time interval greater than one quarter of a wavelength of the unfocused pulses divided by a velocity of the medium. In such embodiments, the method may further include using a compressive sensing technique for generating the Doppler samples.

In some embodiments, the B-mode burst includes one or more focused pulses, individual ones of the focused pulses being transmitted along an axial line within the FOV for generating B-mode image data associated with a single image line in the FOV. In such embodiments, the transmitting of ultrasound pulses may include repeating the sequence until a sufficient number of pulses for generating B-mode image data for all image lines in the FOV have been transmitted. In other embodiments, the second pulses may include unfocused pulses, which may have the same or different properties (e.g., wavelength, frequency, intensity) than the unfocused pulses of the Doppler bursts. In some embodiments, each Doppler burst may include a greater number of transmit pulses than the B-mode burst.

Any of the methods described herein may be embodied in executable instructions stored on non-transitory computer-readable medium communicatively coupled to an ultrasound system, which when executed by the ultrasound system, cause the system to perform the method embodied thereon.

The ultrasound imaging system of the invention is configured for ultrafast imaging, the system comprising:

a transducer array configured to transmit ultrasound pulses toward a medium and receive ultrasound echoes responsive to the pulses;

a transmit controller configured to cause the transducer array to transmit a plurality of ultrasound pulses toward a medium, wherein the plurality of ultrasound pulses includes a regularly repeated sequence comprising a Doppler burst of M unfocused first pulses and a B-mode burst of N second pulses, where M is 2 or more and N is 1 or more; and to cause the transducer array to detect echoes responsive to the transmitted sequence, wherein the detecting includes sequentially detecting, within a field of view, FOV, of the array, first echoes each of which is responsive simultaneously to a set of M of the unfocused first pulses, and detecting a B-mode image frame comprising the echoes of multiple B-mode bursts in the sequence;

processing circuitry including a Doppler processor and a B-mode processor, wherein the processing circuitry is configured to generate Doppler data from signals representative of the first echoes, and to generate B-mode image data from signals representative of the B-mode image frames; and a display configured to simultaneously display the Doppler data and the B-mode image data.

According to some embodiments, an ultrasound system may include a transducer array configured to transmit ultrasound pulses toward a medium and receive ultrasound echoes responsive to the pulses and a transmit controller configured to cause the transducer array to transmit a sequence of pulses comprising a Doppler burst including a plurality of unfocused first pulses followed a B-mode burst including one or more second pulses and to cause the probe to simultaneously detect, within a field of view (FOV) of the transducer array, echoes corresponding to the unfocused first pulses. The system may further include processing circuitry including a Doppler processor and a B-mode processor. The processing circuitry may be configured to receive signals responsive to echoes from the transducer array, where the signals include first echo signals corresponding to the unfocused first pulses and second echo signals corresponding to the one or more second pulses. The Doppler processor may be configured to generate Doppler signals based on the first echo signals, and the B-mode processor may be configured to generate B-mode image data based on second echo signals representative of echoes received responsive to the one or more second pulses, and the system may further include a display configured to simultaneously display the Doppler data and the B-mode image data.

In some embodiments, the system may include a pulse sequence generator. The pulse sequence generator may be communicatively coupled to the transmit controller and may be configured to generate the sequence of pulses and transmit commands to the transmit controller for controlling the array in accordance with the sequence. In some embodiments the sequence of pulses may include a plurality of Doppler bursts and a plurality of B-mode bursts such that all of the first pulses in a given Doppler burst are transmitted within an intra-sample time interval which is less than one eight of a wavelength of the unfocused pulses divided by a velocity of the medium. In some embodiments, the sequence of pulses may be further configured such that successive Doppler bursts are temporally spaced by an inter-sample time interval which is less than one quarter of the wavelength divided by the velocity. In some embodiments, each of the B-mode bursts in the sequence may include a maximum number of second pulses transmittable within a remaining interval of the inter-sample time interval between successive Doppler bursts. In some embodiments, the sequence of pulses may include a plurality of Doppler bursts and a plurality of B-mode bursts, each B-mode burst comprising one or more focused pulses configured to acquired B-mode image data along a single image line in the FOV, and the plurality of B-mode bursts may include a sufficient number of B-mode bursts for generating B-mode image data for all image lines in the FOV.

In some embodiments, the Doppler processor may be configured to generate a Doppler sample based on first echo signals associated with a single Doppler burst. In some embodiments, the Doppler processor may be configured to use a same set of first echo signals associated with a given Doppler pulse for generating multiple Doppler samples. In some embodiments, the Doppler processor may be configured to use first echo signals associated with multiple Doppler bursts to generate a single Doppler sample.

DETAILED DESCRIPTION OF EMBODIMENTS

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

As described, ultrafast imaging is an imaging technique in which a full image can be reconstructed from a single transmit pulse e.g., through the use of parallelized processing of all image lines in the field of view. For example, during ultrafast imaging, a single plane wave may be used to insonify a region of interest and an image of the whole region may be generated from this single insonification.

However, B-mode images generated from the field of view insonifications of ultrafast imaging typically have reduced SNR, low resolution, and grating lobe artifacts. In some situation, multiple planes (e.g., pulsed plane waves) may be used to improve the quality of the image.

Figure 8:
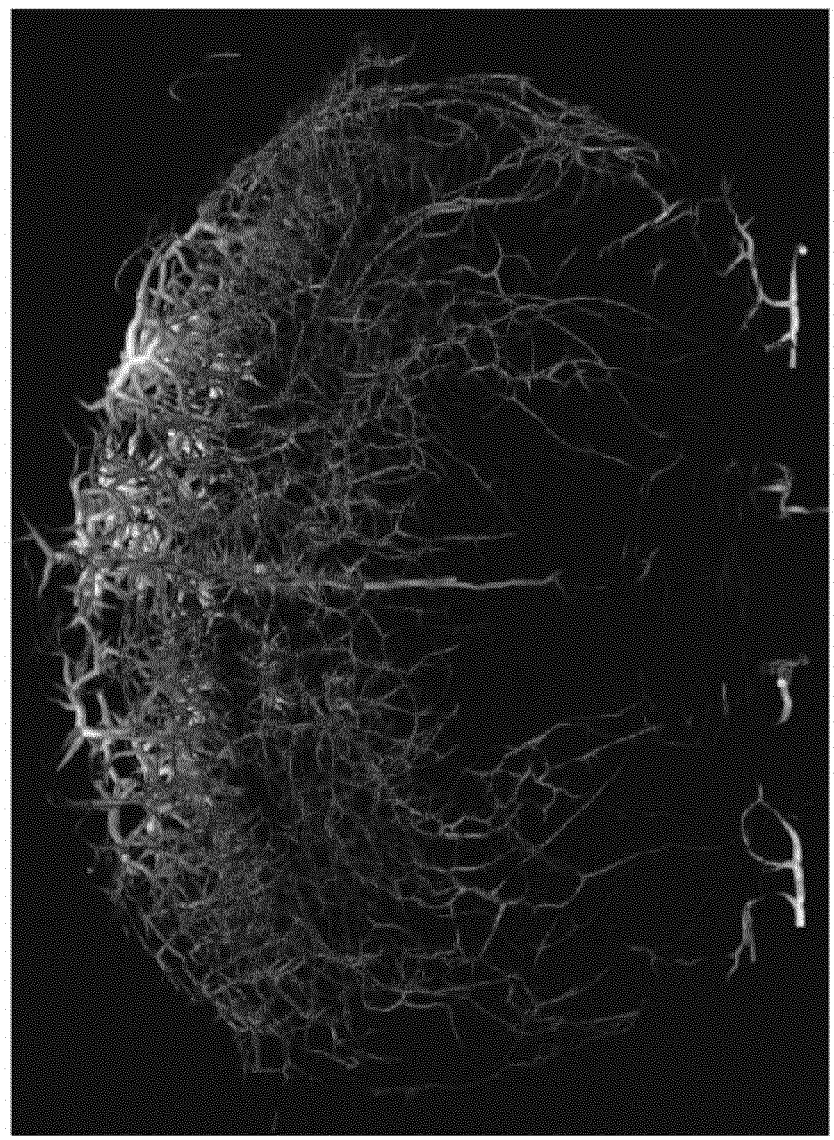
FIG. 8 shows a 3D image of the rat brain vasculature obtained using stacked 2D ultrafast Doppler images according to known techniques, and in which notably anatomical context is lacking.

In existing implementations of ultrafast Doppler imaging (also referred to as continuous Doppler), the techniques do not employ specific B-mode pulses. Anatomical context is generally not provided (as shown in FIG. 8). Rather, if the user wishes to visualize the anatomy as well as well as Doppler data, the same pulses that are used for the Doppler image are used to generate B-mode image data. This approach yields suboptimal B-mode images because the signal-to-noise ratio (SNR), resolution, and frame rate requirements are different for B-mode and for Doppler. Typically very few pulses are coherently compounded for Doppler in order to be fast enough to maintain the required temporal sampling. This can yield low SNR, low resolution and grating lobe artefacts that can be detrimental to the B-mode. The temporal sampling requirements for Doppler are generally greater than for B-mode. When Doppler pulses are used to produce B-mode images, temporal averaging is typically used to regain some SNR. However angular spectrum undersampling and/or reduced angular spectrum span typically used for ultrafast Doppler will hurt image quality in the form of grating lobes and loss in resolution, respectively. In addition, one may want to use different waveforms for Doppler and B-mode pulses. In conventional Doppler modes, pulses are typically more narrowband and slightly lower frequency than B-mode pulses to optimize for sensitivity and penetration.

To address one or more of these problems, the inventors have developed a system and method for configuring pulse sequences that interleave Doppler and B-mode pulses and thereby obtain improvements in duplex B-mode with ultrafast Doppler imaging. Before discussing specific examples of interleaved pulse sequences, some requirements for the Doppler and B-mode pulses will be reviewed.

Ultrafast Doppler Pulses

For continuous Doppler imaging, several plane waves can be combined to enhance SNR and spatial resolution of the signal. Typically, the number of pulses that can be combined is limited by the motion. In other words, after a certain amount of time, beams stop interfering constructively and thus cannot be combined. The time interval $\Delta T_{xbr}$ within which pulses must be sent to be able to combine them constructively is bound by:

$$\Delta T_{xbr} < \frac{\lambda_d}{8v_d}, \qquad \text{(Equation 1)}$$

where $\lambda_d$ is the wavelength of the Doppler pulses and $v_d$ is the maximum expected axial velocity of the flow being measured. The time interval $\Delta T_{xbr}$ defined by Equation 1, which may interchangeably be referred to herein as the intra-sample time interval, is twice shorter than the temporal sampling requirement for acquiring Doppler data without aliasing, which is typically governed by:

$$\Delta T_d < \frac{\lambda_d}{4v_d} \qquad \text{(Equation 2)}$$

The time interval $\Delta T_d$ may be interchangeably referred to herein as inter-sample time interval. Note that if the system employs a nonaliasing displacement estimator (e.g., cross-correlation), then the only requirement is that the clutter filter is effective, which yields:

$$\Delta T_d < \frac{\lambda_d}{2v_d} \quad \text{(Equation 3)}$$

Figure 1:
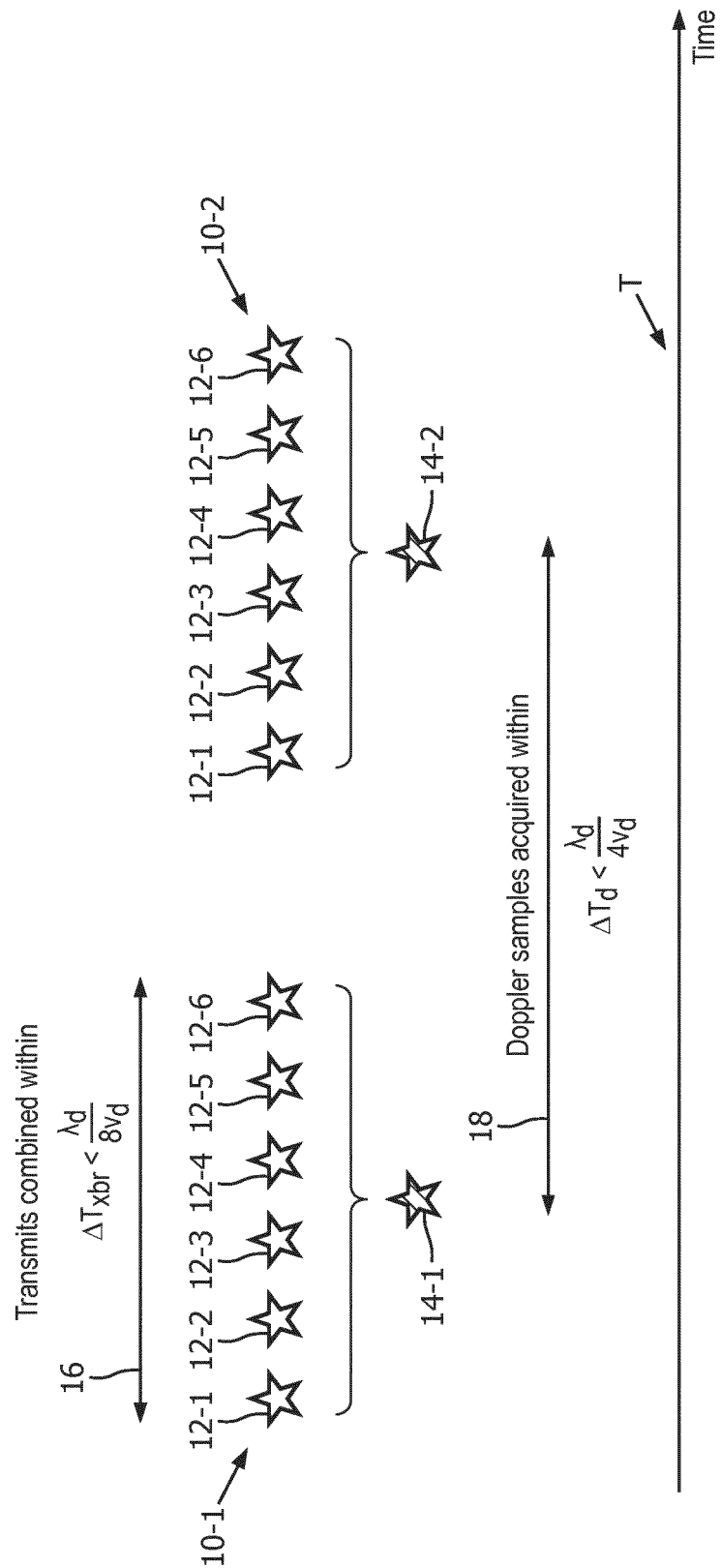
FIG. 1 illustrates a sequence of Doppler pulses for ultrafast Doppler imaging in accordance with the present disclosure.

In summary, for continuous acquisition (e.g., ultrafast Doppler imaging), transmits (i.e., transmit pulses) to be coherently combined may be sent in an interval of time $\Delta T_{xbr}$ (given by Equation 1), yielding one Doppler sample. Consecutive Doppler samples, in turn, may be acquired within $\Delta T_d$ of each other, given by Equation 2 or 3. For simplicity, acquisition using Equation 2 is described herein, but it is understood that Equation 3 may be applied. These pulse sequence configuration parameters are summarized visually in FIG. 1, which shows a first plurality 10-1 of Doppler transmit pulses 12-1 through 12-6 used to acquire a first Doppler sample 14-1 and second plurality 10-2 of Doppler transmit pulses 12-1 through 12-6 used to acquire a second Doppler sample 14-2, as well as the intra-sample time interval 16 and the inter-sample time interval 18 illustrated in relation to a temporal reference frame (e.g., time axis T). FIG. 1 shows a first Doppler burst 10-1, which includes a plurality of Doppler pulses 12-1 through 12-6 (shown as white stars) and a second Doppler burst 10-2 which also includes a plurality of Doppler pulses (e.g., Doppler pulses 12-1-12-6, again shown as white stars). FIG. 1 also shows Doppler samples 14-1 and 14-2 (shown as diagonal line-filled stars), each of which includes the Doppler pulses within the bracket associated with the corresponding Doppler burst (e.g., 10-1 and 10-2, respectively).

B-Mode Pulses

The B-mode pulses can include focused or unfocused pulses, for example unfocused pulses in the form of plane waves (to be coherently combined) or focused pulses or waves (to be coherently or not coherently combined). Similar to the concept described above, the maximum time interval between the first and last B-mode pulses to be coherently combined while maintaining constructive interference between the pulses may be defined by:

$$\Delta T_{Bmode} < \frac{\lambda_b}{8v_b}, \quad \text{(Equation 4)}$$

where $\lambda_b$ is the wavelength of the B-mode pulses and $v_b$ is the maximum expected axial velocity of the tissue being imaged. Note that this number can be significantly higher than the number of Doppler pulses to be combined coherently, because the velocity $v_b$ is typically much lower than the flow velocity $v_d$. Therefore, the sending of B-mode pulses to be combined can be interleaved with the sending of coherent Doppler packets. In fact, as many B-mode pulses or twice as many B-mode pulses can be interleaved while still being able to estimate velocities. It should be noted also that it is not necessary to combine B-mode transmits. In order to have a fully sampled transmit field (yielding optimal resolution and no grating lobes) the number of transmits per B-mode frame may be limited to $D/(\lambda F\#)$ if transmit combination is used, twice that if the transmits are not coherently combined, where D is the lateral extent of the field of view, and $\lambda$ is the imaging wavelength and F# is the F-number (transmit focal depth divided by probe aperture).

Systems and methods for duplex B-mode and ultrafast Doppler imaging in accordance with the present disclosure may operate to transmit sequences of pulses, in which Doppler pulses for continuous Doppler imaging are interleaved with B-mode pulses. The Doppler pulses for continuous Doppler imaging may be arranged such that they satisfy Equations 1 and 2, discussed above. This can be achieved for example with the pulses sequences described further below with reference to FIGS. 3 and 4. Before discussing specific examples of pulse sequences, an exemplary ultrasound system in accordance with the present disclosure is described with reference to FIG. 2.

Figure 2:
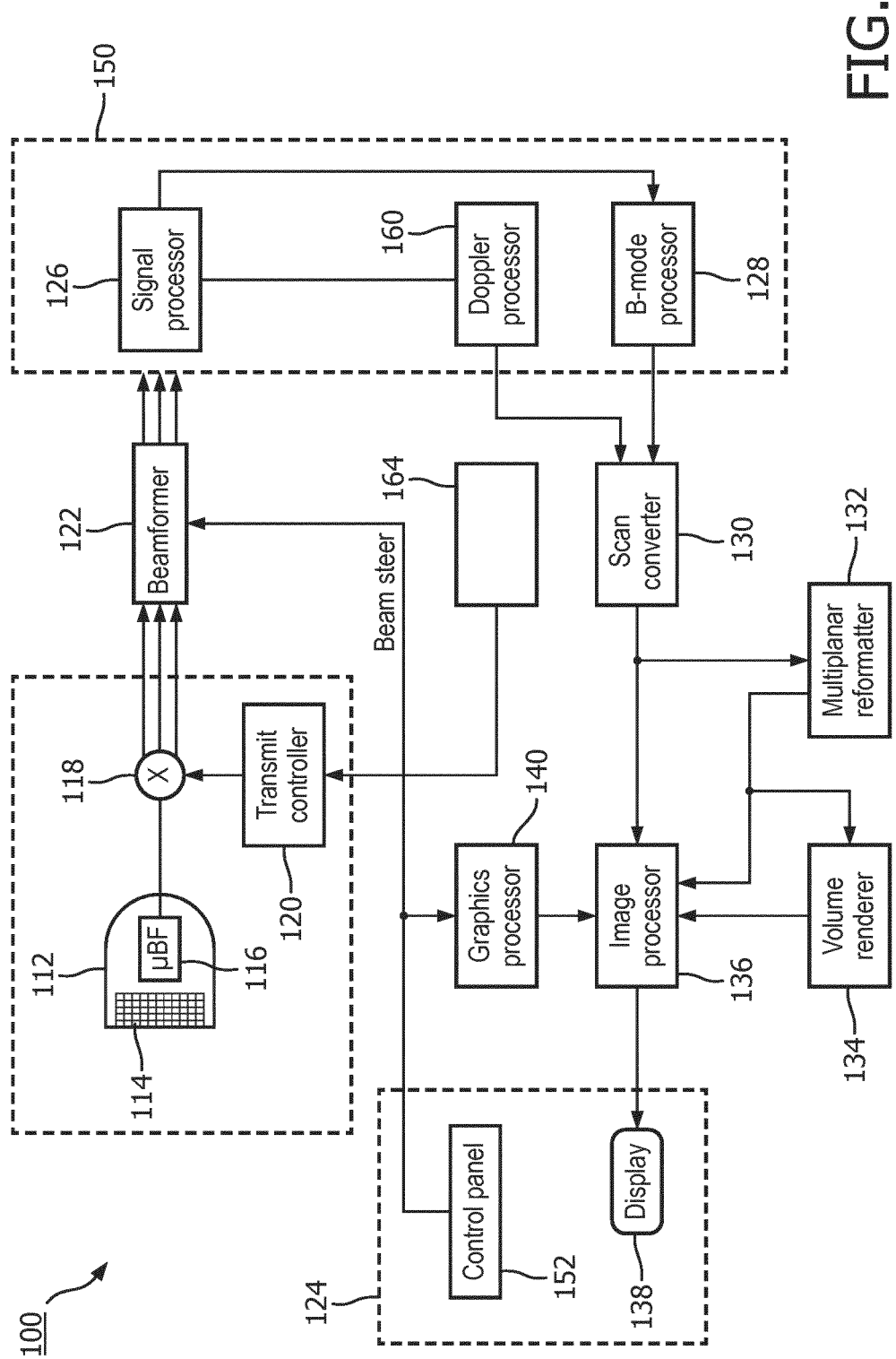
FIG. 2 is a block diagram of an ultrasound imaging system for duplex B-mode and ultrafast Doppler imaging in accordance with the present disclosure.

FIG. 2 shows a block diagram of an ultrasound imaging system 100 constructed in accordance with the principles of the present disclosure. The ultrasound imaging system 100 may be configured to perform conventional B-mode and Doppler imaging, as well as imaging in ultrafast mode, including duplex B-mode with ultrafast Doppler imaging in accordance with the examples herein. In some embodiments, the ultrasound imaging system 100 may be configured to interleave Doppler and B-mode pulses in accordance with the examples herein.

The ultrasound imaging system 100 in the embodiment in FIG. 2 includes an ultrasound probe 112, which includes a transducer array 114 for transmitting ultrasound waves (e.g., ultrasound pulses which may include focused and unfocused pulses) and receiving echoes responsive to the ultrasound waves. In some embodiments, the array may be incorporated into a transducer probe or it may be an ultrasound patch, e.g., of a flexible array, a large area array, or a multi-patch array. The array of the probe 112 may be configured to transmit any combination of pulsed waves including unfocused waves (e.g., plane or diverging waves), which may be tilted or angled, and focused waves, which may be steered. A variety of transducer arrays may be used, e.g., linear arrays, curved arrays, or phased arrays. The transducer array 114, for example, can include a two dimensional array (as shown) of transducer elements capable of scanning in both elevation and azimuth dimensions for 2D and/or 3D imaging. As is generally known, the axial direction is the direction normal to the face of the array (in the case of a curved array the axial directions fan out), the azimuthal direction is defined generally by the longitudinal dimension of the array, and the elevation direction is transverse to the azimuthal direction. The transducer array 114 is coupled to a microbeamformer 116, which may be located in the ultrasound probe 112 or other structure (e.g., in the case of an array which is not incorporated into a probe). The microbeamformer 116 controls transmission and reception of signals by the transducer elements in the array 114. In some examples, the array 114 need not be incorporated in a probe but may be the array of a patch, e.g., a single or multi-patch array, which may be configured to at least partially conform to the subject and/or provide one, two or three degrees of freedom of positional adjustability of individual patches.

In some embodiments, the microbeamformer 116 may be coupled by a probe cable to a transmit/receive (T/R) switch 118, which switches between transmission and reception and protects the main beamformer 122 from high energy transmit signals. In some embodiments, for example in portable ultrasound systems, the T/R switch 118 and other elements in the system can be included in the ultrasound probe 112 rather than in a separate ultrasound system base. The ultrasound system base typically includes software and hardware components including circuitry for signal processing and image data generation as well as executable instructions for providing a user interface.

The transmission of ultrasonic pulses from the transducer array 114 may be controlled by the microbeamformer 116, which may be controlled by the transmit controller 120. The transmit controller 120 may be coupled to the T/R switch 118 and the beamformer 122. In some embodiments, the transmit controller 120 may be coupled to the beamformer 122 using a parallel data transfer link which is configured to transmit simultaneously data for multiple or all image lines in a field of view or from multiple or all points within the field of view of the array, such as during ultrafast scanning. In such embodiments, the array 114 may operate to simultaneously detect echoes along multiple axial lines or points, in some cases all axial lines or all points, within a field of view FOV of the array. In some embodiments, echoes may be detected along only a single or small number of axial lines or points and data transfer between the probe and system base may be performed in serialized fashion according to conventional techniques. The transmit controller 120 may also be coupled to the user interface 124 and receive input from the user's operation of a user controls. The user interface 124 may include one or more input devices such as a control panel 152, which may include one or more mechanical controls (e.g., buttons, encoders, etc.), touch sensitive controls (e.g., a trackpad, a touchscreen, or the like), and other known input devices.

In some embodiments, the transmit controller 122 may also be coupled to a pulse sequence generator 164. The pulse sequence generator 164 may be configured to generate, in part based on system parameters and/or user inputs, a pulse sequence for duplex B-mode with ultrafast Doppler imaging, as described herein. During duplex B-mode and ultrafast Doppler imaging, dedicated transmit pulses for B-mode and for Doppler imaging are transmitted in an interleaved manner, in accordance with a pulse sequence generated by the pulse sequence generator 164, e.g., in accordance with the examples herein including the examples described further with reference to FIGS. 3-6. The pulse sequence generator 164 may be configured to generate a sequence of pulses and cause the transmit controller 122 to control the array 114 to fire the elements of the array in a sequence including at least one Doppler burst followed by at least one B-mode burst. As discussed, the time intervals for interleaving of the pulses may be dependent on parameters such as the wavelength and the velocity of tissue to be imaged, which in the case of B-mode imaging is significantly greater than that of moving tissue (e.g., blood or mechanically stimulated tissue in the case of elastography) and therefore the B-mode pulses can be transmitted over an extended time interval (e.g., over the span of multiple B-mode bursts) while Doppler samples may be generated more frequently.

In some embodiments, the B-mode transmit pulses may have different waveform than the Doppler transmit pulses. For example, relatively more narrowband and lower frequency pulses may be used for the Doppler transmit pulses as compared to the B-mode pulses. Accordingly, the pulse sequence generator 164 sends commands to the transmit controller 122 which then controls the voltage and sequence of firing of the elements of the array 114 as needed to produce the desired sequence of pulses. In some examples, the Doppler pulses may include unfocused pulses (e.g., several plane waves) transmitted within the time interval discussed above the echoes responsive to which may be combined constructively in a Doppler sample. The B-mode pulses may include one or more unfocused pulses (e.g., plane waves), which may be coherently combined, or one or more focused pulses (i.e., focused waves) which may be either coherently or non-coherently combined to form scan lines of the B-mode image. In some cases, a relatively larger number of unfocused pulses may be included in a Doppler burst (e.g., as compared to a B-mode burst) and echoes from multiple pulses may be used to generate a single Doppler sample. In some cases, a relatively fewer number of unfocused pulses may be included in a B-mode burst and echoes from one or more bursts may be used to improve the resolution of the B-mode image.

The user interface 124 may be configured to display an interface e.g., for selecting a duplex B-mode with ultrafast Doppler imaging mode as well as to display overlay images of B-mode and Doppler image data as is conventionally known. Upon selection of the duplex B-mode with ultrafast Doppler imaging mode, the system may automatically select and/or configure the pulse sequence as appropriate. In some embodiments, the user interface may provide one or more controls to enable the user to further tailor the pulse sequence for the duplex B-mode with ultrafast Doppler imaging mode.

Another function which may be controlled by the transmit controller 120 is the direction in which beams are steered. Beams may be steered straight ahead from (orthogonal to) the transducer array 114, or at different angles for a wider field of view. In some embodiments, the partially beamformed signals produced by the microbeamformer 116 may be coupled to a main beamformer 122 where partially beamformed signals from individual patches of transducer elements may be combined into a fully beamformed signal. The beamformed signals are coupled to processing circuitry 150, which may a signal processor 126, a B-mode processor 128, a Doppler processor 160, or combinations thereof. In some embodiments, such as during ultrafast imaging, signals from the beamformer 122 are coupled to the processing circuitry 150 via a parallel communication data link (e.g., a parallel bus) for processing multiple or all image lines at the same time.

The signal processor 126 can process the received echo signals in various ways, such as bandpass filtering, decimation, I and Q component separation, and harmonic signal separation. The signal processor 126 may also perform additional signal enhancement such as speckle reduction, signal compounding, and noise elimination. The processed signals may be coupled to a B-mode processor 128 for producing B-mode image data. The B-mode processor can employ amplitude detection for the imaging of structures in the body. The signals produced by the B-mode processor 128 may be coupled to a scan converter 130 and a multiplanar reformatter 132. The scan converter 130 is configured to arrange the echo signals in the spatial relationship from which they were received in a desired image format. For instance, the scan converter 130 may arrange the echo signal into a two dimensional (2D) sector-shaped format, or a pyramidal or otherwise shaped three dimensional (3D) format. The multiplanar reformatter 132 can convert echoes which are received from points in a common plane in a volumetric region of the body into an ultrasonic image (e.g., a B-mode image) of that plane, for example as described in U.S. Pat. No. 6,443,896 (Detmer). A volume renderer 134 may generate an image of the 3D dataset as viewed from a given reference point, e.g., as described in U.S. Pat. No. 6,530,885 (Entrekin et al.).

In some embodiments, the signals from the signal processor 126 may also be coupled to a Doppler processor 160, which may be configured to estimate the Doppler shift and generate Doppler image data. The Doppler image data may include color data which is then overlaid with B-mode (i.e. grayscale) image data for display. The Doppler processor 160 may be configured to filter out unwanted signals (i.e., noise or clutter associated with non-moving tissue), for example using a wall filter. The Doppler processor 160 may be further configured to estimate velocity and power in accordance with known techniques. For example, the Doppler processor may include a Doppler estimator such as an auto-correlator, in which velocity (Doppler frequency) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators.

In some examples, the velocity and power estimates may undergo further threshold detection to further reduce noise, as well as segmentation and post-processing such as filling and smoothing. The velocity and power estimates are then mapped to a desired range of display colors in accordance with a color map. The color data, also referred to as Doppler image data, is then coupled the scan converter 130 where the Doppler image data is converted to the desired image format and overlaid on the B-mode image of the tissue structure containing the blood flow to form a color Doppler overlay image.

Output (e.g., B-mode images, Doppler images) from the scan converter 130, the multiplanar reformatter 132, and/or the volume renderer 134 may be coupled to an image processor 136 for further enhancement, buffering and temporary storage before being displayed on an image display 138. A graphics processor 140 may generate graphic overlays for display with the images. These graphic overlays can contain, e.g., standard identifying information such as patient name, date and time of the image, imaging parameters, and the like. For these purposes the graphics processor may be configured to receive input from the user interface 124, such as a typed patient name or other annotations. In some embodiments, one or more functions of at least one of the graphics processor, image processor, volume renderer, and multiplanar reformatter may be combined into an integrated image processing circuitry (the operations of which may be divided among multiple processor operating in parallel) rather than the specific functions described with reference to each of these components being performed by a discrete processing unit. Furthermore, while processing of the echo signals, e.g., for purposes of generating B-mode images or Doppler images are discussed with reference to a B-mode processor and a Doppler processor, it will be understood that the functions of these processors may be integrated into a single processor.

Figure 3:
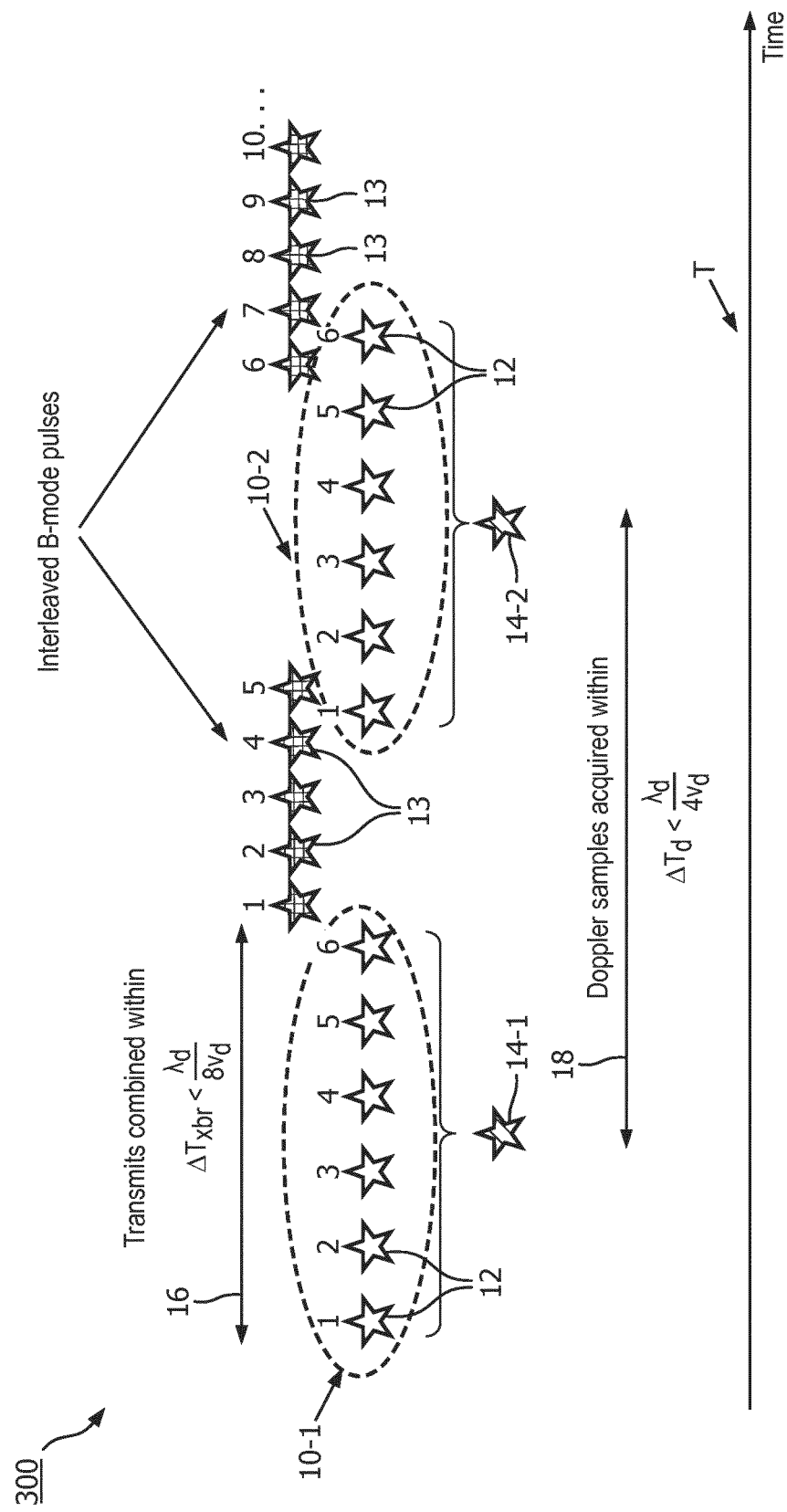
FIG. 3 illustrates an example of a sequence of interleaved Doppler and B-mode pulses in accordance with the present disclosure.
Figure 4:
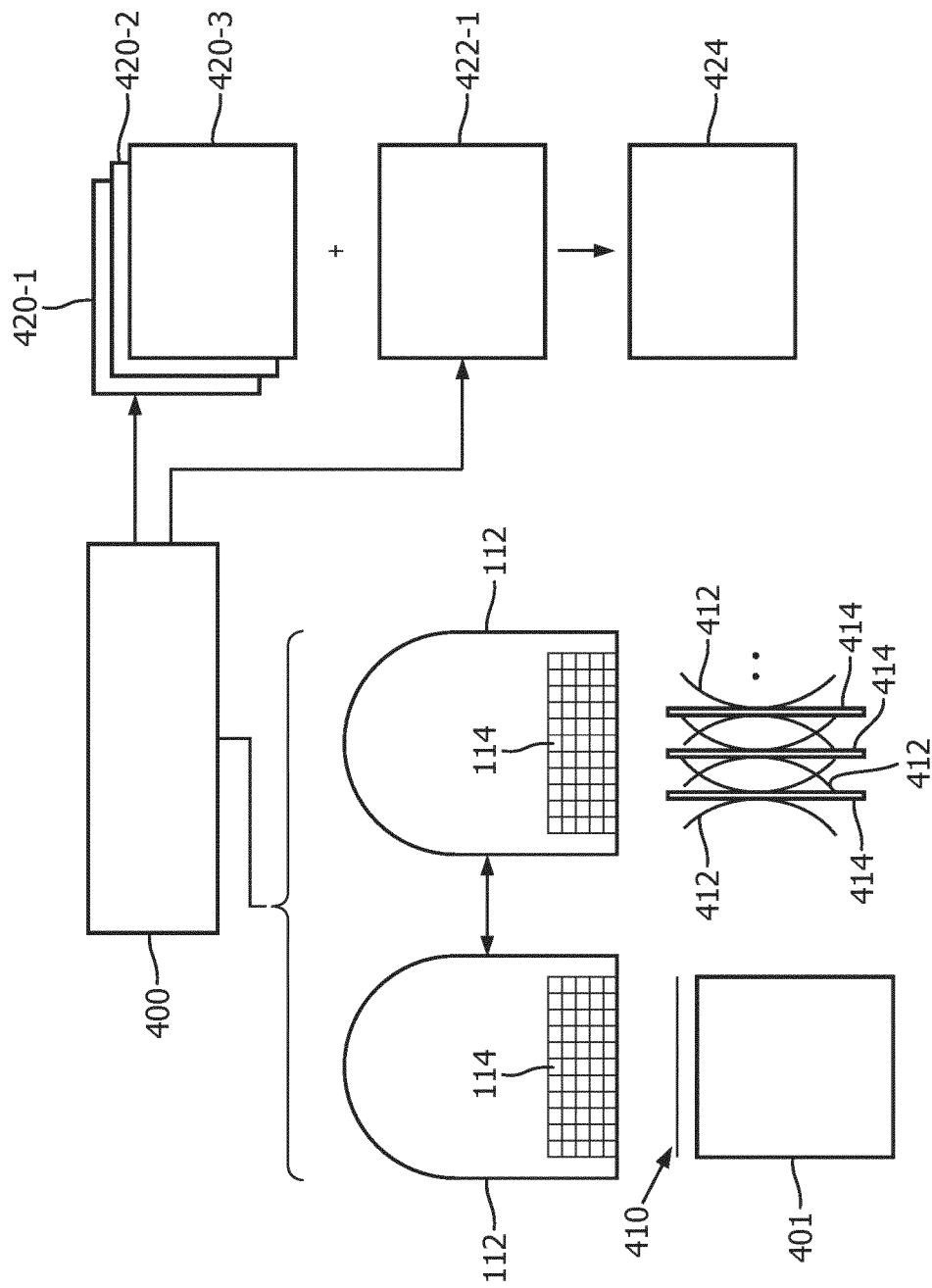
FIG. 4 is a block diagram illustrating ultrasound imaging system configured to perform a sequence of interleaved Doppler and B-mode pulses for duplex B-mode and ultrafast Doppler imaging in accordance with the present disclosure.
Figure 5:
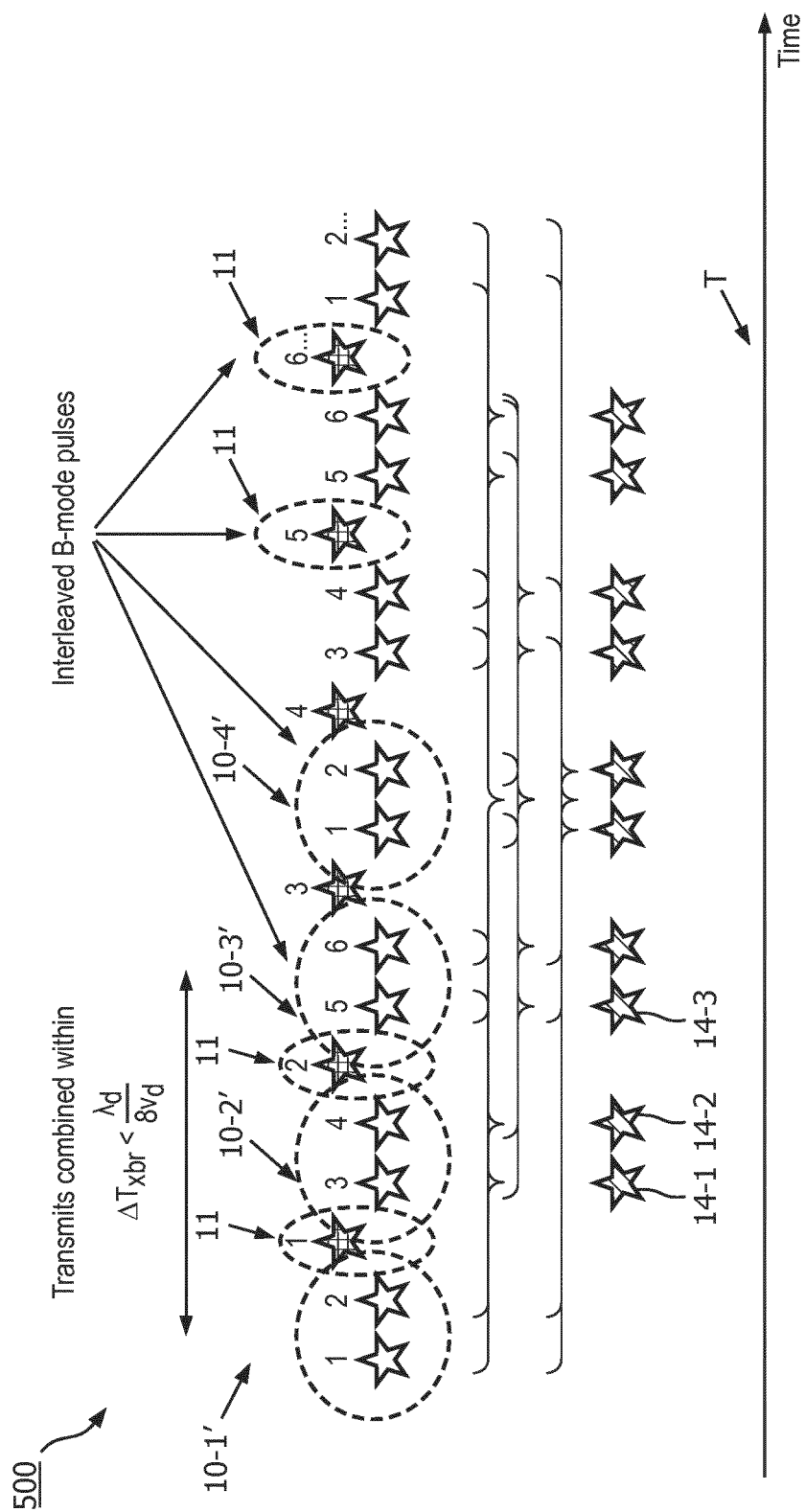
FIG. 5 illustrates another example of a sequence of interleaved Doppler and B-mode pulses in accordance with the present disclosure.

Examples of interleaved pulse sequences in accordance with the principles of the present invention are described further with reference to FIGS. 3-5.

Example 1

FIG. 3 illustrates an example pulse sequence for interleaved B-mode and Doppler pulses which enable continuous Doppler acquisition in accordance with the principles of the present invention. FIG. 3 shows a first Doppler burst 10-1 (indicated by the dashed line), which includes a plurality of Doppler pulses 12-1, 12-2 etc. (shown as white stars) and a second Doppler burst 10-2 (again indicated by the dashed line) and which also includes a plurality of Doppler pulses 12-1, 12-2 etc. (shown as white stars). FIG. 3 also shows a plurality of B-mode pulses 13-1, 13-2, 13-3 and so on (shown as dot-filled stars) and interleaved with the Doppler bursts 10-1 and 10-2. Specifically, in the example in FIG. 3, five B-mode pulses are interleaved between each Doppler burst; however it will be understood that a different number of five B-mode pulses may be interleaved between the Doppler bursts in other examples. Sampling of the Doppler pulses are indicated as Doppler samples 14-1 and 14-2 (shown as diagonal line-filled stars), and include the Doppler pulses within the corresponding bracket. The process depicted in FIG. 3 is described in more detail hereinafter.

In the example in FIG. 3, each burst of Doppler pulses is used to form an entire image. For example, each Doppler burst may include a plurality of unfocused pulses (e.g., plane or diverging waves), each of which may insonify the entire field of view (FOV) of the probe. Each pulse results in a set of echoes (e.g., along all axial lines in the FOV) being detected by the probe and the echoes from the sets associated with all of the Doppler pulses in the burst are combined to form a single Doppler sample and thus obtain a single Doppler frame. In contrast, a burst of B-mode pulses, for example when focused waves are used for the B-mode pulses, may form just part of the B-mode image. That is, the first B-mode pulse 13-1 may be configured to scan a first image line in the FOV and each successive pulse 13-2 through 13-10 and so on may be configured to scan another image line in the FOV until all image lines for generating a full B-mode frame have been acquired. As illustrated, multiple Doppler bursts 10-1, 10-2, and so on, are transmitted during the time interval necessary to scan all image lines with the above described B-mode pulses. The temporal separation between the B-mode pulses used to acquire a single B-mode frame is acceptable because the B-mode image data can be acquired more slowly than Doppler image data, as discussed above e.g., with respect to Equations 1 and 4. In some embodiments, individual transmit pulses may have different tilt angles (in the case of plane wave imaging) or azimuthal direction (in the case of focused wave imaging).

In some embodiments, unfocused pulses (e.g., plane or diverging waves) may also be used for the individual B-mode pulses 13 in each B-mode burst. As will be appreciated, when unfocused pulses are used for B-mode imaging, the entire B-mode image may be formed responsive to a single pulse. In some embodiments, the echoes from multiple unfocused B-mode pulses may be combined in order to enhance the resolution (e.g., SNR) of the B-mode image.

As illustrated in FIG. 3, a first example sequence may include the transmission of a first plurality of Doppler pulses followed by a first plurality of B-mode pulses, then a second plurality of Doppler pulses followed by a second plurality of B-mode pulses, and so on. Each grouping of Doppler pulses that is temporally spaced from another grouping of Doppler pulses by a grouping of one or more B-mode pulses is referred to as a Doppler burst and similarly, each grouping of one or more B-mode pulses that is temporally separated from another grouping of one or more B-mode pulses by a grouping of Doppler pulses is referred to as a B-mode burst. Each Doppler burst may include a plurality of pulses, each of which may be configured to insonify the full FOV of the probe. It is not necessary that each Doppler pulse cover the full FOV, but each Doppler burst must, since the Doppler sample is obtained from only the pulses of one burst, in this example. Individual ones of the B-mode pulses in a burst may, but need not, insonify the full FOV. Depending on the type of waveform used for B-mode imaging, such as when focused waves are used for the B-mode pulses, the sequence of a Doppler burst followed by a B-mode burst may be repeated until all B-mode image lines (i.e. the full B-mode image) have been acquired, which may require for example 64-512 lines to be scanned and thus 64-128 B-mode pulses 13 to be transmitted, depending on desired resolution and/or capability of the array and system. For example, if a scanner has receive beamforming capability for four lines in parallel, then it can form 512 A-lines out of 128 transmit events, as 4 lines are beamformed per transmit event. It will be appreciated that during the time it takes for a full B-mode image to be acquired, the system would continue to acquire Doppler data. Doppler data (e.g., spectral Doppler or color Doppler data) is generated from echoes responsive to the Doppler pulses and B-mode image data is generated from echoes responsive to the B-mode pulses. Thus because a greater number of Doppler samples are acquired during the time necessary to acquire a single B-mode frame (e.g., when imaging with focused B-mode pulses), the Doppler sampling rate, which in continuous (aka ultrafast) Doppler equals the frame rate (i.e., the frequency at which the Doppler frames are updated) may be higher than the B-mode frame rate. In other examples, B-mode imaging may occur in continuous or ultrafast mode such as when unfocused waves are used for the B-mode pulses. In such examples, the Doppler frame rates and B-mode frame rates may be similar, but this is not necessarily so.

For example, let us consider a "slow flow" situation where the goal is to be sensitive to slow-moving blood in small vessels to visualize the microvasculature. Say, the maximum velocity we want to measure is 1 cm/s and the imaging depth is 4 cm, and the imaging frequency is 8 MHz (wavelength of 0.2 mm). Accordingly, the pulse repetition interval (PRI) is 50 us (the time it takes for a wave to go the full depth of the field of view and back is 2d/c where c is speed of sound and d is depth. Here 2*4e-2/1.5e3=50 us) and the Nyquist interval (longest PRI acceptable to avoid aliasing is) is 4800 us (per equation 2). Thus 96 pulses are available (4800/50) for each Doppler sample. No more than 48 plane waves can be coherently combined for each Doppler sample (equation 1), so this leaves 48 pulses for building part of the B-mode frame with pulse characteristics optimized for B-mode. A high-quality B-mode frame can be built with 192 B-mode pulses in the time it takes to acquire 4 Doppler samples, for a B-mode refresh rate of 52 Hz. 5-angle spatial compounding could even be added for a B-mode frame rate of 10.4 Hz. If no interleaving is used (current state of the art), only 48 pulses are available for each B-mode frame (the same 48 pulses that are used to build the Doppler samples), their characteristics may not be optimal for B-mode imaging (e.g., no focusing), the B-mode frame rate is higher at 208 Hz, but this is of no clinical interest.

Fast flow situations are such that very little interleaving can be allowed without aliasing, in these situations only one or two plane waves are available for each Doppler sample, and interleaving becomes complicated by the reverberation artefacts of B-mode pulses into Doppler ensembles.

Referring now also to FIG. 4, which shows components of a system configured to interleave Doppler and B-mode pulses in accordance with the present disclosure, the description of the example sequence in FIG. 3 is continued. As shown in FIG. 4, each Doppler burst may include a plurality of plane waves 410 (at the same or varying angles) transmitted toward a medium (e.g., tissue of a subject to be imaged). A first Doppler burst is initially transmitted responsive to control from the transmit controller, which is responsive to commands from the scanner 400. The scanner 400 may include some or all of the components (e.g., pulse sequence generator 164, processing circuitry 150, etc. of imaging system 100). For each pulse, the probe 112 is controlled to fire a specific combination of transducer elements of the array 114, in some examples substantially the full array, to generate a plane wave 410 for insonifying the full field of view 401 of the array 114.

As shown for example in FIG. 3, multiple pulses 12 (each of which be a plane wave 410) are transmitted for each Doppler burst (e.g., transmit bursts 10-1, 10-2), all or a subset of which are used to obtain a Doppler sample for generating a Doppler frame (e.g., Doppler frame 420-1). Successive Doppler bursts are transmitted to obtain additional Doppler samples for generating additional Doppler frames (e.g., Doppler frames 420-2, 420-3). In real-time imaging, the Doppler frames may be updated on the display in real time at a frame rate determined by the specific sequence being used. All of the pulses in any given Doppler burst in the sequence may be transmitted within an intra-sample time interval which is less than one eight of a wavelength of the unfocused pulses divided by a velocity of the medium, as described above with reference to Equation 1. In some embodiments, one or more of the pulses in a burst, typically the first one or two pulses in the burst may be conditioning pulses and the echoes returning from these pulses may be ignored (e.g., not included in the Doppler analysis).

Following the first burst 10-1 of Doppler pulses 12 which is used to acquire a first Doppler sample 14-1, the probe 112 is then controlled (e.g., responsive to the transmit controller, which is responsive to commands from the scanner 400) to transmit a burst of B-mode pulses 13. For the B-mode pulses, different settings may be applied to the array (e.g., different voltage and/or sequence of firing of individual array elements) in order to produce the desired B-mode wave form for each of the B-mode pulses 13. For example, if focused waves 412 are used to scan individual lines 414, subsets of the array elements may be fired during each pulse in sequential order (e.g., moving in the azimuthal direction of the array) to scan the lines associated with a given burst of B-mode pulses. That is, for the example sequence in FIG. 3, for each of the pulses 13-1 through 13-5, a different subset of elements of the array may be fired to scan five lines in the field of view of the array. The echoes for the scanned lines associated with a given burst is processed as conventionally known to obtain gray-scale image data, which is buffered in memory as is conventionally known until the full image is generated for display. Similar to the burst of Doppler pulses, one or more of the B-mode pulses (e.g., the first one or two pulses) may be conditioning pulses and may be ignored by the signal processing circuitry and thus not used for image generation. If conditioning pulses are used, the first non-conditioning pulse may re-scan the same line(s) as the conditioning pulse(s) (e.g., fire the same elements as the conditioning pulse) before moving to the next line in the sequence. Following the first set of B-mode pulses, which in this example produces only a portion of the image, the probe is automatically re-configured and controlled responsive to commands from the scanner 400 to fire the array in a manner suitable for producing the Doppler pulses. For example, the probe 112 again returns to the first configuration in which the probe is operable to transmit plane wave pulses (e.g., six waves in the example of FIG. 3) to acquire the next Doppler sample 14-2. Successive Doppler bursts may be temporally spaced by an inter-sample time interval which is less than one quarter of the wavelength divided by the velocity, as described above with reference to Equation 2. As shown, the inter-sample time interval which is about 2 times the intra-sample interval provides a time interval between the successive Doppler bursts during which B-mode pulses may be transmitted. In some examples, the number of B-mode pulses transmitted in a single burst is selected to be the maximum number of B-mode pulses that can be transmitted during any remaining time interval between successive Doppler bursts. The maximum number of pulses may depend on various pulse parameters (e.g., wavelength, transmit frequency, depth of imaging, etc.) and thus a different maximum number may be applicable depending on the specific B-mode pulses used.

Following acquisition of the second Doppler sample 14-2, the probe 112 again transitions to the second configuration in which B-mode pulses (e.g., focused waves) are transmitted to now scan the next few image lines for the B-mode image frame 422-1. All image lines for a single B-mode frame are thus acquired over a time interval during which multiple Doppler samples, in some cases 10, 20 or more Doppler samples, and thus multiple frame have been acquired enabling continuous Doppler data to be overlaid on high resolution B-mode images. The overlay image 424, which may include a single frame (e.g., single B-mode and Doppler frame) or a cineloop in which the Doppler data and B-mode data are updated at their respective rates, may be displayed as is conventionally known on a display of the scanner 400.

In some examples, such as the example in FIG. 3, only echoes responsive to a single Doppler burst are used in generating Doppler data for any given Doppler sample. In other examples, echoes from multiple Doppler bursts may be combined to form a single Doppler sample. As will be appreciated, the specific number of pulses shown in FIG. 3 (e.g., six pulses for each Doppler burst and five pulses for each B-mode burst) are illustrative only. In other example, a different number of pulses may be used in either of the Doppler and B-mode bursts as long as the Doppler pulses used to acquire any given sample are temporally spaced according to the sample interval ($\Delta T_d$). In some embodiments, fewer than six Doppler pulses (for example four pulses or five pulses) or greater number of Doppler pulses (7 or more) may be used for each Doppler burst. In the case of the latter, fewer number of B-mode pulses may be used in each B-mode burst to maintain the required temporal spacing between the individual Doppler bursts. In yet further examples, different number of B-mode pulses may be used in each burst and/or different interleaving of B-mode pulses may be utilized, for example as described further below with reference to FIG. 5.

Example 2

FIG. 5 illustrates another example pulse sequence 500 for interleaved B-mode and Doppler pulses that enable continuous Doppler acquisition and which may provide higher resolution B-mode images as compared to conventional continuous Doppler imaging techniques. Similar to FIG. 3, Doppler bursts 10-1', 10-2', 10-3', etc., each include a plurality of Doppler pulses (shown by the white stars), in this example two pulses per burst as indicated by the dashed lines around each grouping of Doppler pulses. B-mode pulses (shown by the dot-filled stars) are interleaved with the Doppler bursts. In the illustrated example, each individual B-mode burst 11 includes a single B-mode pulse; however different number of B-mode pulses may be included in a B-mode burst in accordance with other examples. FIG. 5 also shows Doppler samples 14-1, 14-2, 14-3, which in this example are produced from Doppler pulses associated with multiple Doppler bursts (as indicated by the brackets above each of the diagonal line-filled stars.

As shown in FIG. 5, the B-mode pulses may preferably be more frequently interleaved, which may enable a greater number of Doppler samples to be acquired. As compared to the example in FIG. 3 where a total of 22 pulses were transmitted producing two Doppler samples, in this example for a total of 20 pulses, 10 Doppler samples can be acquired. Assuming, for purposes of this example, that each pulse is in the form of a plane wave, which insonifies the full field of view and thus can produce echoes which can be used to generate a full image, up to six Doppler pulses may be combined to acquire a single Doppler sample or frame. This is because any five adjacent Doppler pulses are transmitted within the time interval $\Delta T_{xb_r}$ that meets the requirements discussed herein. Specifically, echoes responsive to pulses 1 and 2 from the first Doppler burst 10-1', pulses 3 and 4 from the second Doppler burst 10-2', and pulse 5 and 6 from the third Doppler burst 10-3' can be combined to form a first Doppler sample 14-1. The echoes from pulse 2 from the first Doppler burst 10-1', pulses 3 and 4 from the second Doppler burst 10-2', pulses 5 and 6 from the third Doppler burst 10-3', and pulse 1 from the fourth Doppler burst 10-4', can be combined for the second Doppler sample 14-2. Continuing in a similar manner, the pulses from the second and third Doppler bursts (3 through 6) and pulses 1 and 2 of the fourth Doppler burst (10-4') can be combined to form the third Doppler sample 14-3, and so on. B-mode bursts 11 are interleaved between each Doppler burst (e.g., between each pair of Doppler pulses).

Here, Doppler samples are formed responsive to pulses associated with different Doppler bursts but because the bursts are more closely temporally spaced, pulses from multiple bursts are combined to form a single Doppler sample. Also, because the B-mode pulses are more frequently interleaved, a greater number of Doppler samples may be acquired and spaced closely together. The interleaving of B-mode pulses in this manner causes the Doppler samples to be irregularly spaced, but the missing samples can be recovered through interpolation. Similar as in the previous example, B-mode images are acquired much more slowly than Doppler samples, as their temporal sampling requirements are not as strict.

Similar to FIG. 3, the sequence in FIG. 5 shows only part of the full sequence (e.g., covering only 6 lines of the B-mode image) as may be required to obtain a full B-mode image. Also, as discussed above with respect to FIG. 3, the Doppler bursts and/or the B-mode bursts may include conditioning pulses that are not used for image data generation. In such examples, the interleaving may be modified. In some examples, each Doppler burst may include 2 pulses as shown, and each B-mode burst may include two pulses, the first pulse of each burst being a B-mode conditioning pulse. In another example, each Doppler burst may include 3 pulses, the first of which may be a Doppler conditioning pulse, and each B-mode burst may include 2 pulses, the first of which may be a B-mode conditioning pulse. In this example, four successive Doppler pulses can be used to form a Doppler sample, the first pulse being ignored and the remaining three pulses used for Doppler data analysis. For the B-mode image data generation each first pulse in each burst is ignored and each second pulse of each burst is used to scan a single line thus the sequence is repeated at least a number of times required to scan all image lines.

For example, let us consider again the "slow flow" situation where the goal is to be sensitive to slow-moving blood in small vessels to visualize the microvasculature. The maximum expected velocity is 1 cm/s, the imaging depth is 4 cm, and the imaging frequency is 8 MHz (wavelength of 0.2 mm). Accordingly, the pulse repetition interval (PRI) is 50 us as earlier (determined by the travel time of sound waves to the maximum imaged depth and back) and the Nyquist interval (longest PRI acceptable to avoid aliasing is) is 4800 us (per equation 2). Thus 96 pulses are available (4800/50) for each Doppler sample, and Doppler pulses to be combined into one sample should not be separated by more than 48 pulses (equation 1). For example, the following sequence can be considered: angles 1-12 for a Doppler sample, followed by lines 1-4 of the B-mode image, angles 13-24 of Doppler, lines 5-8 of B-mode, angles 25-36 of Doppler, lines 9-12 of B-mode, angles 1-8 of Doppler, lines 13-18 of B-mode . . . and so on until 192 B-mode lines have been acquired. The advantage is a faster Doppler sampling rate which is beneficial for Doppler SNR (more samples are available per unit of time and can thus be averaged). The disadvantage is more back and forth between Doppler and B-mode pulses, and a slower B-mode refresh rate (17 Hz in this particular example, still largely acceptable clinically).

Again, fast flow situations are such that very little interleaving can be allowed without aliasing, in these situations only one or two plane waves are available for each Doppler sample, and interleaving becomes complicated by the reverberation artefacts of B-mode pulses into Doppler ensembles.

In cases where the interleaving of B-mode pulses leads to temporal undersampling of the Doppler signal, compressed or compressive sensing (also known as compressive sampling or sparse sampling) may be used for Doppler estimation. Compressive sensing for recovering Doppler samples in a sparse sequence may be performed in accordance with the technique described by J. Richy et al in "Blood Velocity Estimation Using Compressive Sensing," published in IEEE Transactions on Medical Imaging Vol. 32, No. 11, November 2013, pp 1979-88, the full content of which is incorporated herein by reference in its entirety for any purpose.

Figure 6:
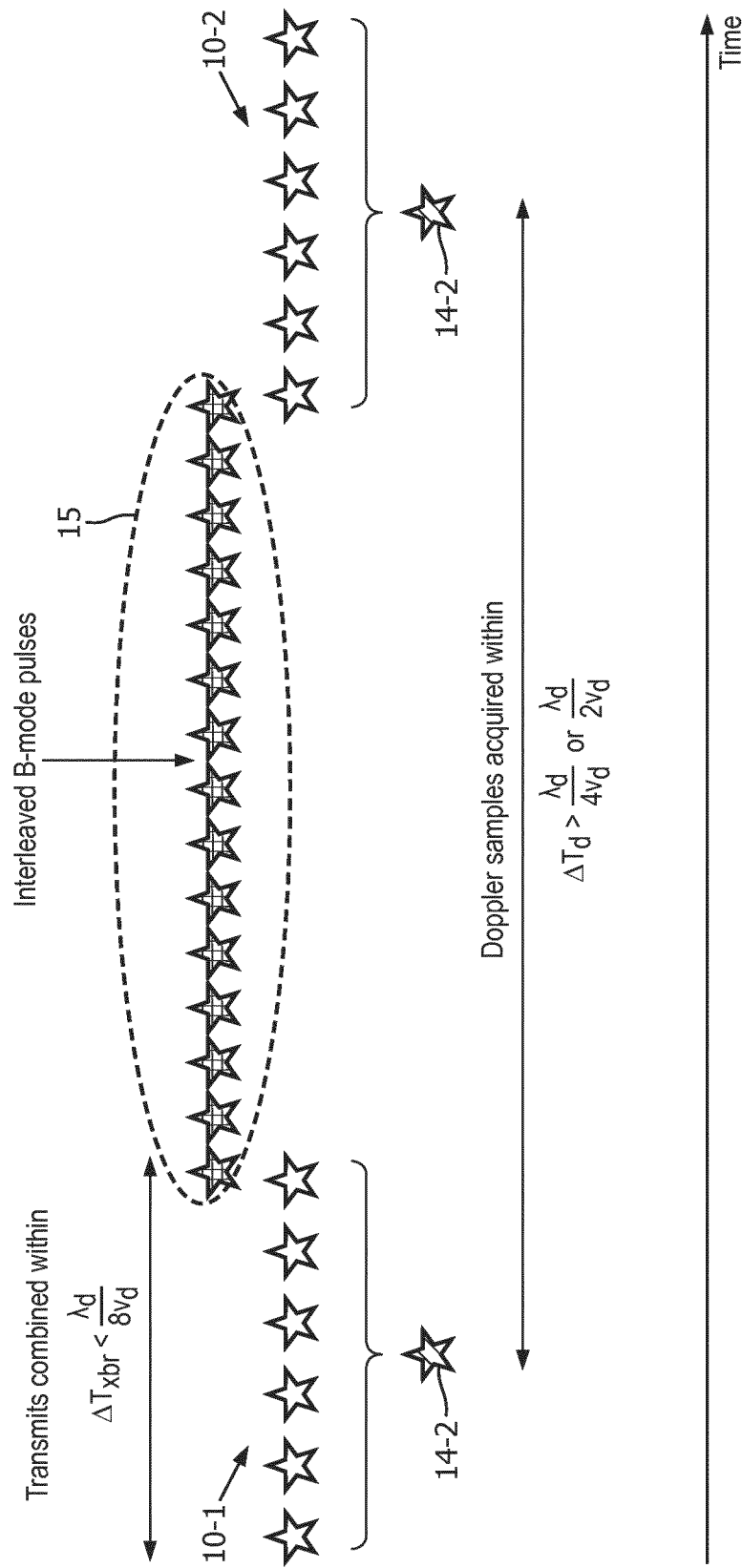
FIG. 6 illustrates yet another example of a sequence of interleaved Doppler and B-mode pulses in which Doppler signals may be undersampled and where compressive sensing may be used to recover the Doppler velocity in accordance with the present disclosure.

In accordance with further embodiments, ultrasound pulses may be transmitted in a sequence which includes a plurality of Doppler bursts temporally spaced by a time interval which is greater than one quarter of the wavelength of the transmit pulses divided by the maximum velocity of the medium. In such embodiments, the method may further include using a compressive sensing technique for generating the Doppler samples. For example, as shown in FIG. 6, the requirement to satisfy Equation 2 may be relaxed by using compressed or compressive sensing for Doppler estimation. In this example, Doppler samples 14-1, 14-2 are acquired at a rate slower than Nyquist, which allows the user to use longer B-mode packets or bursts 15 to improve the quality of the B-mode images. In the specific illustrated example, each repetition or burst of Doppler pulses 10-1, 10-2 includes six pulses with a greater number of B-mode pulses 15 (e.g., six or more and in this particular case fifteen pulses) being transmitted between successive Doppler bursts. Compressive sensing may be used to retrieve the Doppler velocity. Although compressive sensing techniques are known and are in themselves outside of the scope of the present invention, a brief explanation is provided. Generally, compressive sensing Doppler estimation works by assuming that the Doppler signal (flow+clutter) is modelled by a sum of a few sinusoids (or wavelets). Mathematically, one wants to find the $a_k$'s and $\omega_k$'s (i.e. the spectral decomposition) that minimize the difference between the sparsely measured signal s(t) and the sparse signal model, by solving:

$$E = \int_t |s(t) - \Sigma a_k e^{i\omega_k t}|^2 + \mu \Sigma |a_k| \qquad \text{(Equation 5)},$$

where μ is the penalization term that adjusts the tradeoff between sparsity and fidelity of the reconstructed signals. This energy is typically minimized numerically, yielding the Doppler spectrum. From the Doppler spectrum, a 2D Doppler display can be derived, as well as retrospective spectral Doppler at each point in the image. Note that the reconstruction works best if the time interval between consecutive (sparse) Doppler samples is pseudo-random as a regular, sparse sampling introduces artifacts.

Figure 7A:
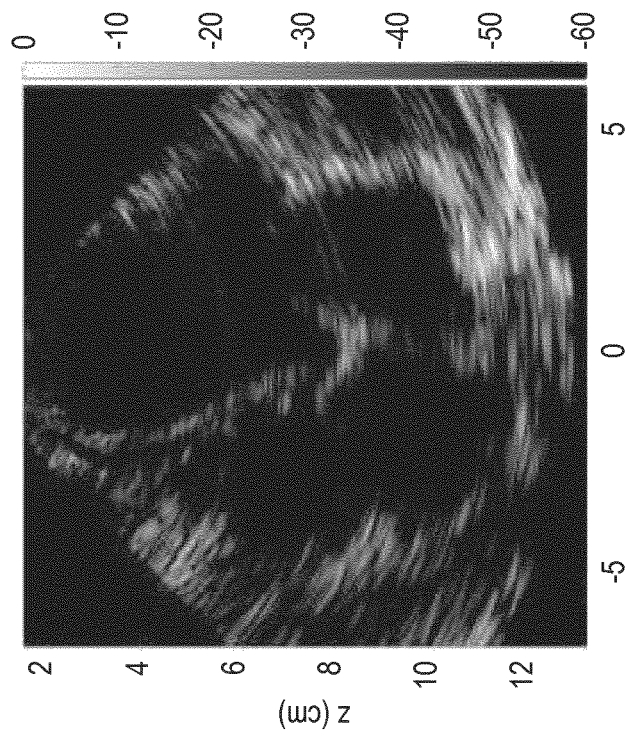
FIGS. 7A and 7B show cardiac 4-chamber B-mode images pre and post reconstruction with compressive beamforming.
Figure 7B:
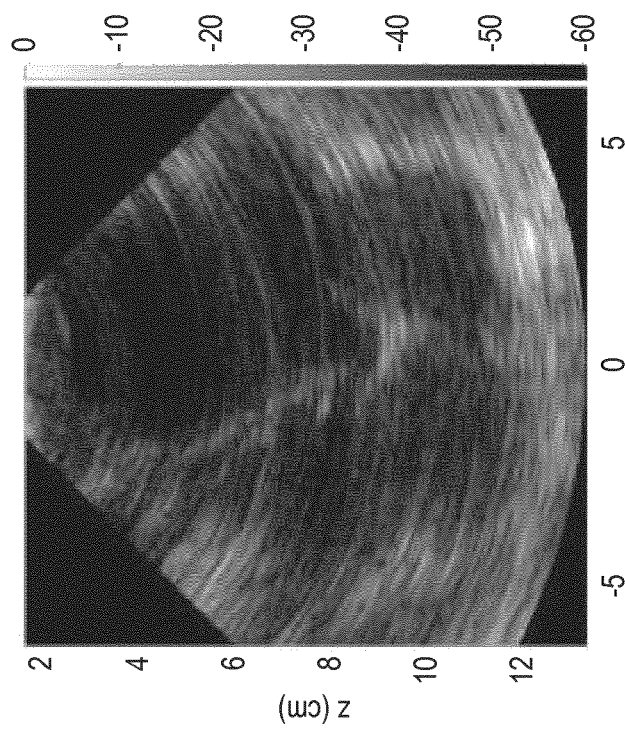

Conversely, if the B-mode pulses are spatially undersampled, compressive beamforming is used to restore the quality of the B-mode images. In some cases, one will be constrained both in Doppler acquisition speed and B-mode acquisition speed and only a small number of transmits can be used to reconstruct the B-mode images. In that case, compressive beamforming may be used to restore good image quality (see e.g., FIG. 7A, which shows cardiac 4-chamber image acquired with a single diverging transmit beam and 7B, which shows the same data following compressive beamforming reconstruction). Compressive beamforming technique, which in themselves are outside of the scope of the present invention, are generally known and an example of such technique is described by B. Zhang, J. L. Robert and G. David in "Dual-Domain Compressed Beamforming for Medical Ultrasound Imaging," published in IEEE IUS Conference, 2015, the full content of which is incorporated herein by reference in its entirety for any purpose.

Alternatively to compressive sensing, in cases where Doppler sampling is slow and does not satisfy the Nyquist sampling criterion (equation 2), other nonaliasing estimators known in the field can be used to estimate blood velocity. These include, but are not limited to, cross-correlation-based motion tracking, and spatio-temporal phase unwrapping of the Doppler angles.

Any pulse sequence which interleaves Doppler and B-mode pulses in accordance with the present invention, for example the sequences 300 and 500, may be programmed in the pulse sequence generator 164 for generating commands which may cause the transmit controller 120 to control the firing of the array elements of probe 112. In some examples, the pulse sequence generator 164 may additionally or alternatively be programmed with pulse generation logic which implements the requirements for interleaving additional pulses (e.g., B-mode pulses) with Doppler pulses for continuous Doppler imaging, as described with reference to FIG. 1, and Equations 1-3. In this manner, depending on the system parameters (e.g., pulse wavelength, pre-programmed velocity values or ranges for blood flow) and/or user specified parameters (e.g., user specified velocity for moving tissue to be imaged), the pulse sequence generator 164 may automatically generate an interleaved sequence which satisfies the requirements discussed herein and apply commands to the transmit controller when the user is operating the system in the duplex B-mode with ultrafast Doppler imaging mode.

Figure 9:
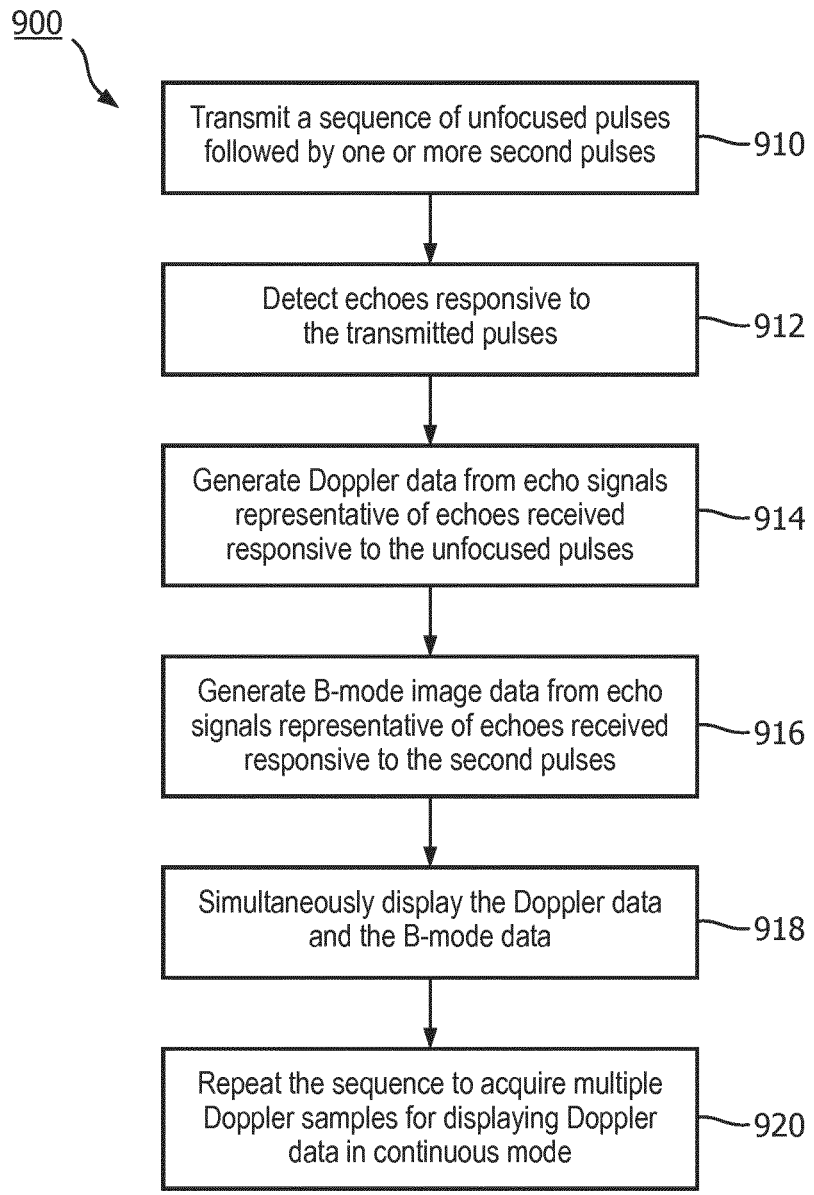
FIG. 9 is a flow diagram of a process for duplex B-mode and ultrafast Doppler imaging in accordance with the present disclosure.

FIG. 9 shows a flow diagram of a process 900 in accordance with the present disclosure. The process 900 may include transmitting, using an ultrasound probe, a plurality of ultrasound pulses toward a medium (e.g., tissue of a subject to be imaged). The plurality of ultrasound pulses may be transmitted in a sequence of a Doppler burst comprising a plurality of unfocused first pulses followed a B-mode burst comprising one or more second pulses, as shown in block 910. In some examples, all of the first pulses in a given Doppler burst may be transmitted within an intra-sample time interval which is less than one eight of a wavelength of the unfocused pulses divided by a velocity of the medium. In some examples, successive Doppler bursts may be temporally spaced by an inter-sample time interval which is less than one quarter of the wavelength divided by the velocity.

The method may further include detecting echoes responsive to the transmitted pulses, as shown in block 912. Echoes may be detected responsive to each of the pulses in the Doppler and B-mode burst. Echoes are typically detected after each pulse is transmitted, thus each transmit pulse is typically followed by a receive (or listen) period during which a set of echoes responsive to a given pulse are detected and corresponding set of echo signals associated with the given pulse are generated. The echo signals are transmitted for signal processing (e.g., for generation of Doppler and B-mode data). In the case of serialized processing of the echo signals, the image data for each line may be buffered before the image is displayed. In the case of ultrafast imaging, the detecting of echoes may include simultaneously detecting a set of echoes from the entire insonified region (e.g., multiple echoes along multiple axial lines within a field of view (FOV)) and responsive to each pulse, and simultaneously transmitting the corresponding echo signals to the processing circuitry (e.g., signal processor 126, B-mode processor 128, Doppler processor 160) for Doppler estimation and B-mode image data generation.

As shown in in blocks 916 and 918, the method may continue by generating Doppler data from the echo signals associated with the Doppler bursts and generating B-mode image data from the echo signals associated with the B-mode bursts. In some embodiments, the sets of echo signals associated with a given Doppler burst may be used to generate one Doppler sample. In some embodiments, only sets of echo signals that are associated with a given Doppler burst may be used to generate a given Doppler sample. In some embodiments, sets of echo signals associated with a plurality of Doppler burst may be used to generate one Doppler sample. In some embodiments, a set of echo signals received responsive to a Doppler burst may be used multiple times (e.g., coherently combined) for generating a plurality of Doppler samples. In other words, in some embodiments, two or more Doppler samples may be based, at least in part, on echo signals received responsive to the same Doppler burst.

In some embodiments, the sequence of Doppler burst followed by B-mode burst may be repeated in order to acquire multiple Doppler samples for displaying Doppler data in continuous mode, as shown in block 910. In some embodiments, in which the B-mode bursts include one or more focused pulses, individual ones of the focused pulses may be used for generating B-mode image data associated with a single image line in the FOV. In such embodiments, the transmitting of ultrasound pulses may include repeating the sequence until a sufficient number of pulses for generating B-mode image data for all image lines in the FOV have been transmitted. In other embodiments, the second pulses may include unfocused pulses, which may have the same or different properties (e.g., wavelength, frequency, intensity) than the unfocused pulses of the Doppler bursts. In some embodiments, each Doppler burst may include a greater number of transmit pulses than the B-mode burst, for example two times or greater than the transmit pulses in the B-mode burst.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., a CPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

The invention claimed is:

1. A method of ultrafast imaging, the method comprising:
transmitting a plurality of ultrasound pulses toward a medium from a transducer array, wherein the plurality of ultrasound pulses includes a regularly repeated sequence comprising a Doppler burst of M unfocused first pulses which insonify an entire field of view (FOV) and a B-mode burst of N second pulses, where M is 2 or more and N is 1 or more,
   wherein the unfocused first pulses are transmitted within an intra-sample time interval less than one eighth of a wavelength of the unfocused first pulses divided by an axial velocity of a flow being measured, and
   wherein Doppler bursts of the regularly repeated sequence are temporally spaced by an inter-sample time period less than one quarter of the wavelength divided by the axial velocity of the flow;
detecting echoes responsive to the transmitted sequence, wherein the detecting includes sequentially detecting, within the FOV of the array, first echoes each of which is responsive to the unfocused first pulses in sequential repetitions of the regularly repeated sequence, and detecting a B-mode image data comprising second echoes responsive to multiple B-mode bursts in the sequential repetitions of the regularly repeated sequence;
generating a Doppler sample from a set of the first echoes, the set including the first echoes responsive to unfocused first pulses from two or more of the sequential repetitions of the regularly repeated sequence;
generating Doppler data from signals representative of the Doppler sample;
generating B-mode image frame from signals representative of the B-mode image data; and
simultaneously displaying the Doppler data and B-mode image frame.

2. The method of claim 1, wherein the B-mode bursts include the maximum number of second pulses transmissible within the remaining interval of the inter-sample time interval between successive Doppler bursts.

3. The method of claim 1, wherein the set of the first echoes includes more than M unfocused first pulses from two or more repetitions of the regularly repeated sequence to generate each Doppler sample.

4. The method of claim 3, wherein the Doppler samples are temporally spaced irregularly, and the method includes interpolating between the samples.

5. The method of claim 1, wherein the first pulse transmitted in each burst of the first and/or the second pulses is a conditioning pulse.

6. The method of claim 1, wherein the B-mode second pulses include focused pulses, wherein individual ones of the focused pulses are transmitted along an axial line within the FOV for generating B-mode image data associated with a single image line in the FOV, and wherein the repeated sequence generates the B-mode image frame comprising all the image lines in the FOV.

7. The method of claim 1, wherein the second pulses include one or more unfocused pulses.

8. The method of claim 1, wherein M is greater than N.

9. The method of claim 1, wherein the Doppler transmit pulses have a waveform in a narrower frequency waveband and at a lower frequency than the B-mode transmit pulses.

10. A non-transitory computer-readable medium comprising executable instructions, which when executed on a processor of a medical imaging system cause the medical imaging system to perform the method of claim 1.

11. An ultrasound imaging system configured for ultrafast imaging, the system comprising:
a transducer array configured to transmit ultrasound pulses toward a medium and receive ultrasound echoes responsive to the pulses;
a transmit controller configured to:
cause the transducer array to transmit a plurality of ultrasound pulses toward a medium, wherein the plurality of ultrasound pulses includes a regularly repeated sequence comprising a Doppler burst of M unfocused first pulses and a B-mode burst of N second pulses, where M is 2 or more and N is 1 or more, wherein the unfocused first pulses are transmitted within an intra-sample time interval less than one eighth of a wavelength of the unfocused first pulses divided by an axial velocity of a flow being measured, and wherein Doppler bursts of the regularly repeated sequence are temporally spaced by an inter-sample time period less than one quarter of the wavelength divided by the axial velocity of the flow and
cause the transducer array to detect echoes responsive to the transmitted sequence, wherein the detecting includes sequentially detecting, within a field of view, FOV, of the array, first echoes each of which is responsive to the unfocused first pulses in sequential repetitions of the regularly repeated sequence, and detecting a B-mode image data comprising the echoes of multiple B-mode bursts in the sequential repetitions of the regularly repeated sequence;
processing circuitry including a Doppler processor and a B-mode processor, wherein the processing circuitry is configured to generate a Doppler sample from a set of the first echoes, the set including the first echoes responsive to unfocused first pulses from two or more of the sequential repetitions of the regularly repeated sequence, generate Doppler data from signals representative of the Doppler sample, and to generate B-mode image frame from signals representative of the B-mode image data; and
a display configured to simultaneously display the Doppler data and the B-mode image frame.

12. The system of claim 11, wherein the B-mode bursts include the maximum number of second pulses transmissible within the remaining interval of the inter-sample time interval between successive Doppler bursts.

13. The system of claim 11, wherein the set of first echoes includes more than M unfocused first pulses are used to generate each Doppler sample.

14. The system of claim 13, wherein the Doppler samples are temporally spaced irregularly, and the method includes interpolating between the samples.

15. The system of claim 11, wherein the first pulse transmitted in each burst of the first and/or the second pulses is a conditioning pulse.

16. The system of claim 11, wherein the B-mode second pulses include focused pulses, wherein individual ones of the focused pulses are transmitted along an axial line within the FOV for generating B-mode image data associated with a single image line in the FOV, and wherein the repeated sequence generates the B-mode image frame comprising all the image lines in the FOV.

17. The system of claim 11, wherein the second pulses include one or more unfocused pulses.

18. The system of claim 11, wherein M is greater than N.

19. The system of claim 11, further comprising a pulse sequence generator communicatively coupled to the transmit controller, wherein the pulse sequence generator is configured to generate the sequence of pulses and transmit commands to the transmit controller for controlling the array.

20. The system of claim 11, wherein the Doppler transmit pulses have a waveform in a narrower frequency waveband and at a lower frequency than the B-mode transmit pulses.

* * * * *